(12) United States Patent
Dahlström

(10) Patent No.: US 8,578,781 B2
(45) Date of Patent: Nov. 12, 2013

(54) DEVICE TO INDICATE CRITICAL CORROSION OF A METALLIC STRUCTURE

(75) Inventor: Anders Dahlström, Gustavsberg (SE)

(73) Assignee: SCS Engineering AB, Gustavsberg (SE)

( * ) Notice: Subject to any disclaimer, the term of this patent is extended or adjusted under 35 U.S.C. 154(b) by 204 days.

(21) Appl. No.: 13/255,132

(22) PCT Filed: Apr. 19, 2010

(86) PCT No.: PCT/SE2010/050417
§ 371 (c)(1), (2), (4) Date: Oct. 4, 2011

(87) PCT Pub. No.: WO2010/126429
PCT Pub. Date: Nov. 4, 2010

(65) Prior Publication Data
US 2012/0031188 A1    Feb. 9, 2012

(30) Foreign Application Priority Data
Apr. 30, 2009    (SE) ....................................... 0950289

(51) Int. Cl.
*G01L 7/00* (2006.01)
*G01N 33/00* (2006.01)
*G01N 7/00* (2006.01)
*G01N 17/00* (2006.01)
*G01M 3/02* (2006.01)

(52) U.S. Cl.
USPC ............... 73/700; 73/866; 73/23.2; 73/19.7; 73/37; 73/86

(58) Field of Classification Search
None
See application file for complete search history.

(56) References Cited

U.S. PATENT DOCUMENTS

| | | | | |
|---|---|---|---|---|
| 3,960,496 A * | 6/1976 | Schieber | .......................... | 422/53 |
| 4,043,178 A * | 8/1977 | Winslow, Jr. | .................. | 73/23.2 |
| 4,056,968 A * | 11/1977 | Winslow, Jr. | ................ | 73/19.07 |
| 4,065,373 A * | 12/1977 | Martin et al. | ................. | 204/404 |
| 4,587,479 A * | 5/1986 | Rhoades et al. | ................ | 324/700 |
| 5,392,661 A * | 2/1995 | Freeman | ......................... | 73/866 |
| 5,425,267 A * | 6/1995 | Herrmann et al. | ................ | 73/86 |
| 6,551,552 B1 * | 4/2003 | Lyublinski et al. | ............... | 422/9 |
| 6,946,855 B1 | 9/2005 | Hemblade | | |
| 7,508,223 B1 | 3/2009 | Yang et al. | | |
| 2008/0036476 A1 | 2/2008 | Nielsen et al. | | |

FOREIGN PATENT DOCUMENTS

| | | |
|---|---|---|
| EP | 1 605 247 | 12/2005 |
| JP | 2-107947 | 4/1990 |

OTHER PUBLICATIONS

International Search Report issued on Apr. 27, 2010 in International Application No. PCT/SE2010/050417 filed Apr. 19, 2010.

* cited by examiner

*Primary Examiner* — Andre Allen
(74) *Attorney, Agent, or Firm* — Drinker Biddle & Reath LLP

(57) ABSTRACT

The present invention relates to a device to indicate a predetermined critical corrosion of a metallic structure located in soil, water or concrete environment. The device comprises a probe that has a closed tubular container intended to contain a pressurized medium, and that has a wall thickness t that corresponds to the predetermined critical corrosion. A protective coating is arranged essentially over the entire outside of the container with the exception of a surface that is intended to be subjected to corrosion attack. The container is allowed to corrode so that the container becomes perforated, whereupon the pressure of the pressurized medium falls. The pressure change is measured by means of a pressure gauge, and in this way, information is obtained about the fact that the corrosion has reached the predetermined critical level.

10 Claims, 3 Drawing Sheets

DEVICE TO INDICATE CRITICAL CORROSION OF A METALLIC STRUCTURE

CROSS REFERENCE TO RELATED APPLICATIONS

This application is a §371 National Stage Application of PCT International Application No. PCT/SE2010/050417, filed Apr. 19, 2010, and claims priority under 35 U.S.C. §119 and/or §365 to Swedish Application No. 0950289-9 filed Apr. 30, 2009.

The present invention relates to a device that indicates when exterior corrosion on a metallic structure located in soil, water or concrete and that is subjected to external influence reaches a predetermined depth, i.e., a corrosion critical to the metallic structure.

BACKGROUND

Metallic structures located in soil, water or concrete are always subjected to more or less corrosion. If the construction in addition is subjected to stray currents or another external influence, such as a chloride-containing environment, the corrosion is usually increased. In these cases, the corrosion arises not only in the form of general corrosion but also in the form of localized corrosion, usually pitting, which gives a considerably faster penetration of the construction than general corrosion.

Steel embedded in concrete is generally protected from corrosion by the high alkalinity of the concrete, whereby the steel surface becomes passivated. However, by increased content of chloride of the pore water of the concrete and/or carbonation, which arises because of lowering of the pH value of the concrete as a consequence of the influence of the carbon dioxide of the air, the passivity of the steel may be disrupted and corrosion initiated. Already after a relatively small corrosion attack, cracks arise and then spalling of concrete due to the voluminous corrosion products of the steel. Today, carbonation is a smaller problem, but chloride-initiated corrosion is present to a great extent. Chloride-initiated corrosion is above all a common problem in concrete structures arranged in a marine environment or road environments.

In spite of extensive research, it has not been possible to establish reliable chloride threshold values of when the corrosion is initiated on steel embedded in concrete. Other circumstances such as concrete composition, moisture content, presence of different types of corrosion cells, etc., have influence. This entails great difficulties in condition assessments and thereby to know when, for instance, repair measures should be applied. Measures applied too late may cause security risks and increased repair costs.

Pipe conduits installed in the ground are often buried in the vicinity of power lines in order to in this way utilize the easements that already are there. This makes among other things that stray currents are often found in the vicinity of the pipe conduits.

Pipe conduits installed in the ground and made of steel for oil and gas are usually protected against corrosion by an outer protective coating in combination with a cathodic protection. The protective effect can be checked by a so-called potential measurement. However, in areas of stray currents, there are difficulties to maintain a reliable protection due to strong local variations. Accordingly, in these areas, there is a need of monitoring the corrosion that after all takes place.

Today, modern pipe conduits are provided with an outer coating of thick polyethylene in order to protect against corrosion attacks. However, small mechanical defects inevitably arise in the coating. By this protective coating, the pipe is also insulated against ground, and as a consequence of this, high alternating current potentials may be built up in the pipe conduit due to induction from adjacent power lines. In case of a high alternating current potential on the pipe conduit, alternating currents of a high current density may flow between the pipe and the surrounding soil in coating defects. In case of high alternating current densities, alternating current corrosion arises. This has resulted in serious localized corrosion with perforations as a consequence. Hence, the ambition to minimize the corrosion of pipe conduits by providing them with a protective coating has created a new corrosion phenomenon. In spite of intense research, no reliable criteria have been possible to be established. In certain cases, corrosion arises, in other not.

In order to monitor corrosion of buried pipe conduits, today usually two different techniques are used. The first technique utilizes test plates, which is based on the fact that test plates, weighed in advance, are buried adjacent to the pipe and electrically connected to the pipe. After a certain predetermined time, the plates are dug up and the occurred general and localized corrosion, respectively, of the test plates are evaluated by measuring pit depth and evaluation of mass change, respectively. The technique of employing test plates has, on one hand, economical disadvantages as a consequence of high costs of burying and digging up as well as evaluation, and information about serious corrosion is, on the other hand, often obtained far later than when it has occurred.

The second technique utilizes so-called ER (Electrical Resistance)-probes. ER-probes are based on the principle that the resistance in a wire or a sheet of the metal increases when the amount of metal decreases as a consequence of corrosion. In this case, the rate of corrosion can be measured continuously. ER-probes provide good information about the magnitude of the general corrosion, however no or at least only a very small indication of local corrosion attacks is obtained, such as pitting, since they only marginally have an impact on the total resistance of the wire/sheet. For a pipe conduit, it is the pitting corrosion rate that is the most important parameter, since a local pit may give rise to leakage.

In case of stray current influence, particularly from alternating current, there is a tendency that corrosion attacks become of local character i.e., local pits. As mentioned above, these cannot in a reliable way be recorded by ER-probes. Neither is the technique of employing test plates sufficient and it is expensive, as has been described above.

JP 2107947 discloses a solution to measure corrosion on a metallic buried pipe. A box body comprising closed hollow spaces is buried in the vicinity of the pipe. The box body has a wall thickness that is less than the wall thickness of the metallic pipe. The closed hollow spaces are provided with a pressurized medium having a predetermined pressure via connected conduits. The pressure of the medium is measured by a pressure gauge. When the wall of the box body has corroded so much that a hole has been formed in the wall, the pressure in the closed hollow space will fall, which is detected by means of the pressure gauge. By detecting a reduction of the pressure, information is thus obtained about the wall of the box body having corroded so that the wall has been perforated, and by that the corrosion has reached a critical level.

However, the solution disclosed in JP 2107947 has the disadvantage that it does not reflect the real conditions that the metallic pipe conduit usually is subjected to. According to the solution disclosed in the document, the box body will not be electrically insulated and will accordingly not be subjected to alternating current influence and high current densities in the same way as a metallic pipe having a protective coating.

For protective coated metallic structures that are not cathode protected, in certain cases also moisture may migrate in, for instance, from the soil via a local defect in the protective coating, between the protective coating and the metallic structure, whereby a local corrosion cell may be formed under the coating. This local corrosion cell may give rise to such corrosion that the coating risks peeling off from the surface of the metallic pipe.

SUMMARY OF THE INVENTION

The object of the present invention is to rapidly get an indication of when corrosion, above all localized corrosion such as a pit, attains a predetermined critical level for a pipe conduit installed in the ground or another metallic structure installed in, or in another way in contact with, soil, water or concrete environment.

This is accomplished by the device according to the independent claim 1 as well as the method according to the independent claim 8. Preferred embodiments are defined by the dependent claims.

The device according to the invention comprises a probe that has a closed tubular container intended for a pressurized medium. The container is made of a metallic material, preferably the same or essentially the same as the metallic material that the metallic structure, for which the critical corrosion is to be indicated, is made of. The container has a centre axis, an outside as well as an inside. The inside defines the space that is intended for a pressurized medium. The wall thickness of the container corresponds to the depth of the corrosion that is considered to be critical for the metallic structure, which means that the wall thickness of the container is less than the thickness of the metallic structure, for instance, the wall thickness of a pipe conduit installed in the ground.

The device has also a connection member intended for the connection of the container to a source of pressurized medium. The pressurized medium is supplied to the container from the source via the connection member. The connection member is preferably arranged at or in the vicinity of an end of the tubular container.

The device also comprises means for electrically connecting the container of the probe to the metallic structure where the critical corrosion is to be determined. This guarantees that the container and the metallic structure have the same electric potential and that they accordingly are subjected to the same conditions. This means for electrically connecting the container and the metallic structure to each other may suitably be an insulated conductor.

The container of the probe is coated essentially over the entire outside thereof with a protective coating except over a predetermined surface. This surface is free and will in use accordingly be exposed to the environment that the metallic structure is subjected to and will thereby corrode. Hence, this means that the probe comprises a container having a protective coating that is arranged on the outside of this container and has a controlled defect, and mimics in this way the conditions that the metallic structure in worst cases could be subjected to, i.e., in case of a defect in the coating on the construction.

According to a preferred embodiment, the container is essentially rotationally symmetrical around the centre axis thereof. This guarantees that the container is not subjected to an inhomogeneous current density distribution above all over the surface that is intended to corrode, and that the device thereby in a reliable way indicates the corrosion that the metallic structure can be subjected to.

The probe is placed in the immediate vicinity of the metallic structure where the critical corrosion level is to be determined. By this, the probe is exposed to the same corrosive soil, water or concrete environment as the metallic structure. The other parts of the device may, if desired, be placed remotely from the metallic structure provided that the container is electrically connected to the metallic structure.

Before use, the container is filled up to a positive pressure with a medium, preferably inert gas, via the connection member. It is guaranteed that the pressurized medium cannot escape to the surroundings. Upon use, the pressure is monitored in the container by means of a pressure gauge, such as a manometer or an electric pressure transducer. When the deepest corrosion on the uncoated outside of the container reaches the same depth as the wall thickness, the pressure falls in the container as a consequence of the penetrating corrosion, i.e., perforation of the container. This is detected by means of the pressure gauge, and in such a way information is obtained about the corrosion having reached the predetermined critical level.

The size of the surface that is to be subjected to corrosion is suitably determined by the environment, such as concrete, water or type of soil, and another external influence, for instance, electric influence, that the metallic structure is subjected to. The size of the surface is also suitably determined by the expected occurrence of and the size of defects in a possible coating arranged on the metallic structure. The suitable size of the surface can easily be determined by a person skilled in the art by simple routine tests.

By means of the device according to the invention, it is possible to rapidly get an indication that corrosion of a metallic structure located in soil, water or concrete has reached a predetermined critical level. The device is particularly advantageous since it also will indicate corrosion as a consequence of stray currents, particularly alternating current corrosion. The device is in addition relatively inexpensive to manufacture and does not require that it should be removed from the environment at regular intervals for evaluation. In fact, it only has to be replaced when the corrosion has reached the predetermined critical level, for instance, when it is about time for repair measures of the metallic structure.

LIST OF FIGURES

DETAILED DESCRIPTION

Figure 1:
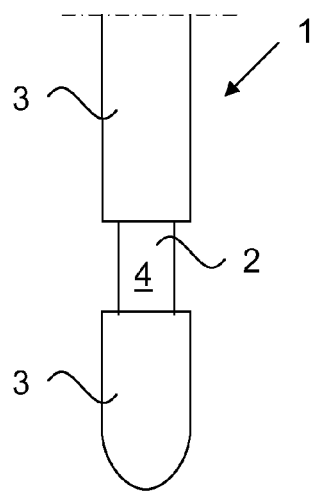
FIG. 1 shows a side view of a part of a probe according to a first embodiment of the device according to the invention.

The present invention relates to a device to indicate a predetermined critical corrosion of a metallic structure installed in, or in another way in contact with, soil, water or concrete environment. The metallic structure may, for instance, be buried in sand, soil or clay, located on the bottom of the sea, subjected to rain, moisture or condensate, or be embedded in concrete. The device comprises a probe that is intended to be subjected to corrosion on a part of the external surface thereof. The probe comprises a closed tubular container intended to contain a pressurized medium when used.

In this connection, a closed container should be considered to be a container that has solid walls essentially around the entire inside thereof with the exception of an inlet opening, and thereby has the possibility of containing a pressurized medium. The inlet opening is arranged in one wall of the container and intended for the introduction of pressurized medium into the interior of the container. The inlet opening may be arranged so that it can be entirely sealed, whereby the container is entirely closed when using the device. However, it is also feasible that the inlet opening always is open to a connection member, as will be described further below.

The container has a centre axis and a first as well as a second end, at least the first end being intended to be placed in the vicinity of the metallic is structure. According to a preferred embodiment, the container is essentially rotationally symmetrical around the centre axis thereof.

The device also comprises a connection member intended for the connection of the container to a source of pressurized medium. The connection member is arranged at the inlet opening of the container. The pressurized medium is supplied to the container from the source via the connection member and the inlet opening of the container. The connection member is preferably arranged at or in the vicinity of the second end of the tubular container. Furthermore, the connection member has a valve that guarantees that the pressurized medium does not flow back from the connection member out toward the source of pressurized medium alternatively the surroundings.

The device also comprises a pressure gauge to measure the pressure of the pressurized medium upon use of the device.

The connection member may in certain cases be arranged so that also the same, at least partly, should contain the pressurized medium upon use of the device, for instance, when the pressure gauge is arranged at a distance from the container. In this case, the connection member also connects the container with the pressure gauge.

In order to guarantee that the container has the same electric potential as the metallic structure, and thereby is subjected to the same conditions as the metallic structure, the device also comprises means for electric connection between the container and the metallic structure. This means for electric connection may, for instance, be one or more conductors that are electrically insulated except where they connect to the metallic structure and the container of the probe, respectively. Of course, also the connecting point between at least the metallic structure and said means for electric connection is preferably insulated against the surroundings in accordance with conventional technique.

On the outside of the container, there is a protective coating arranged essentially over the entire outside of the container with the exception of a predetermined surface. This surface is intended to corrode and is accordingly left free from protective coating. The purpose of the protective coating is to control where the corrosion will occur on the container, as well as to guarantee that the free surface has a size that is adapted to get an influence equivalent to the monitored construction, above all in those cases the device is to be used in environments where stray currents are found. The protective coating has furthermore a purpose of, when using the device to indicate corrosion of a protective coated metallic structure, mimicking the conditions that the metallic structure in fact is subjected to. The protective coating is preferably the same or essentially the same as the protective coating that the metallic structure has. For instance, the protective coating may be polyethylene when the device is to be used for the indication of corrosion of pipe conduits installed in the ground.

The size of the surface that is to be subjected to corrosion is suitably determined by the environment that the metallic structure is subjected to, such as concrete, water or soil. Also other conditions, such as possible electric influence, affect the suitable size of the surface. However, the suitable size of the surface can easily be determined by a person skilled in the art by simple routine tests.

According to one embodiment of the invention, the area of the surface that is intended to corrode is 0.5-10 $cm^2$, preferably 0.5-5 $cm^2$. However, it is feasible that the surface is either smaller or larger depending on the application.

The container is made of a metallic material, preferably the same or essentially the same metallic material as the metallic structure is made of, as well as has a wall thickness that corresponds to the critical corrosion of the metallic structure at least on the surface of the container where the corrosion is meant to occur.

Below, the invention will be described in detail by means of the figures. However, the invention should not be considered to be limited to the embodiments shown in the figures but may be varied within the scope of the independent claims. The figures should not be considered to be true to scale since certain features have been exaggerated in order to more clearly illustrate the invention.

Figure 2:
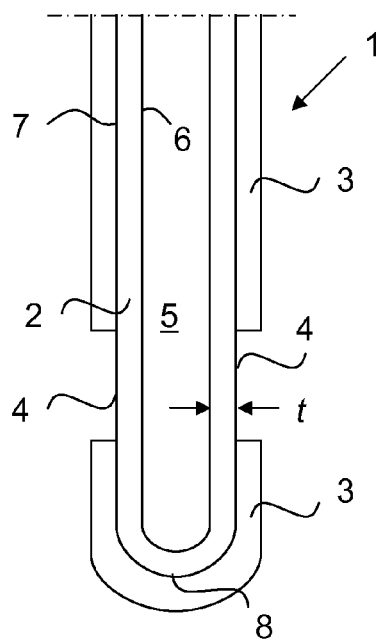
FIG. 2 shows a cross-section of the probe according to FIG. 1.

FIG. 1 shows a side view and FIG. 2 shows a cross-section of a part of the probe 1 according to a first embodiment. The probe 1 comprises a tubular container 2 of a metallic material as well as a protective coating 3 arranged on the outside of this container. The protective coating 3 is arranged essentially over the entire outside 7 of the tubular container with the exception of a surface 4. Hence, the container is provided with a protective coating that has a controlled defect that corresponds to the area at the surface 4, and the container will thereby be subjected to corrosion attack on this surface 4 in use.

The surface 4 has a first extension essentially parallel to the centre axis (not shown) of the tubular container 2 as well as a second extension around the entire circumference of the outside of the container. The surface 4 is arranged at a distance from the first end 8 of the tubular container as well as at a distance from the second end thereof (not shown).

The tubular container 2 has a wall thickness t that corresponds to the depth of the predetermined critical corrosion of the metallic structure that the device is intended to be used for. Hence, this means that the wall thickness t of the container is less than the thickness of the metallic structure. This guarantees that information about the fact that the metallic structure may have corroded to a critical level can be obtained in good time in order to, for instance, enable repairs of the metallic structure before perforation of the metallic structure has occurred.

The inside 6 of the metallic container 2 defines a space 5 intended to contain a pressurized medium. The pressurized medium may be a gas or liquid, however a medium is used that does not risk causing internal corrosion of the container. Preferably, an inert gas is used as the pressurized medium. When using the device according to the invention, the surface 4 will corrode as a consequence of the environment and conditions that it is subjected to. When the corrosion has proceeded so far that perforation of the metallic container has occurred, the pressure of the pressurized medium in the container will fall, which is detected by means of a pressure gauge. In such a way, information is obtained about the fact that the corrosion has reached the predetermined critical level for corrosion of the metallic structure.

According to a preferred embodiment, the tubular container is essentially rotationally symmetrical around the centre axis thereof, i.e., both the inside and the outside of the container are essentially rotationally symmetrical. This makes that a uniform current density distribution is obtained over the surface 4.

Figure 3:
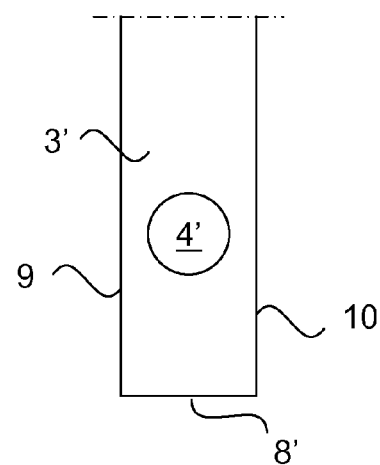
FIG. 3 shows a side view of an alternative embodiment of a probe.

It is also feasible that the container may have a cross-section that is not rotationally symmetrical around the centre axis thereof, for instance, a quadratic or rectangular cross-section perpendicular to the centre axis of the container. When the cross-section of the container is not circularly perpendicular to the centre axis of the container, the current density will however be higher in possible corners of the cross-section of the container that thereby run the risk of corroding considerably faster than the rest of the cross-section of the container. Therefore, in these cases the corners of the cross-section are provided with the protective coating and the surface that is free from coating is arranged on an outer surface of the cross-section at a distance from said corners. In this case, the free surface ought to be essentially circular in order to obtain a uniform current density distribution over the entire surface thereof. FIG. 3 shows a side view of a part of a probe according to this embodiment where the entire container has an essentially quadratic cross-section perpendicular to the centre axis thereof and is coated with the protective coating 3' except over a surface 4' that is essentially circular and arranged at a distance from each edge 9, 10 of the probe as well as at a distance from the one end 8' and the other end (not shown) of the probe.

Figure 4:
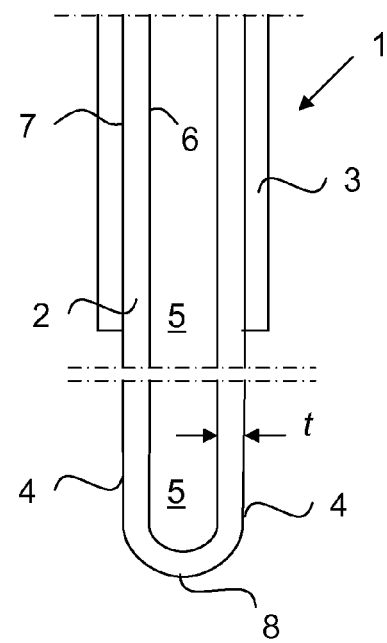
FIG. 4 shows a cross-section of an alternative embodiment of a probe.

FIG. 4 shows a part of a probe 1 according to an alternative embodiment. The probe according to this embodiment differs from the probe according to FIG. 1 in that the container is provided with a protective coating 3 only in the upper part thereof, i.e., the surface 4 that is intended to corrode is arranged essentially at the first end 8 of the tubular container. This embodiment of the probe may, for instance, be suitable in use in environments that do not run the risk of being subjected to stray currents. The probe shown in FIG. 4 may, for instance, be used when the device is to be used to indicate a critical corrosion of a metallic structure in a concrete environment, for instance, reinforcement embedded in concrete.

Figure 5:
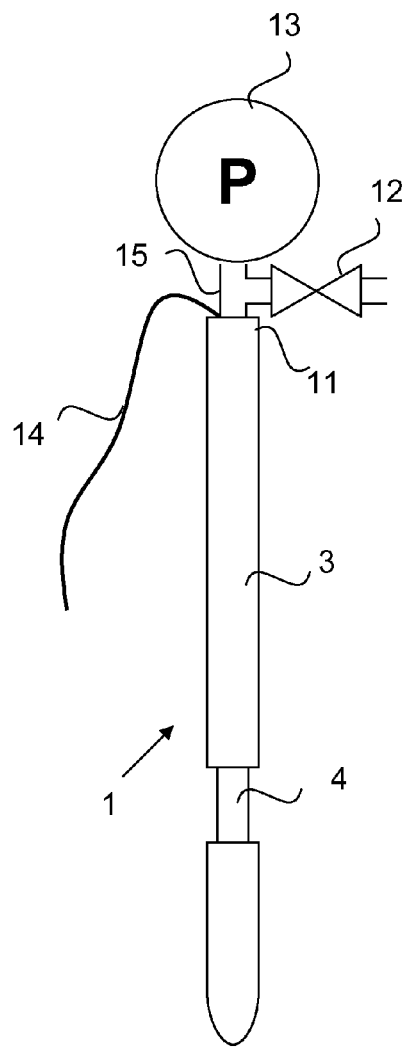
FIG. 5 shows an embodiment of the device according to the invention.

FIG. 5 shows an embodiment of the device according to the invention. The device comprises a probe 1. The probe 1 comprises a tubular container having a protective coating 3 arranged essentially over the entire outside of the tubular container with the exception of a surface 4 that is intended to be subjected to corrosion.

A connection member 15 for the connection of the container to a source of pressurized medium is arranged in the upper end 11 of the container. The connection member 15 comprises a valve 12 intended to be connected to the source for the pressurized medium and to guarantee that pressurized air does not flow from the container out to the surroundings via the connection member 15.

The device also comprises a pressure gauge 13 arranged to measure the pressure of the pressurized medium in the container, as well as means 14 to electrically connect the container to the metallic structure. Means for providing remote monitoring of the pressure gauge can easily be arranged in accordance with conventional technique.

Figure 6:
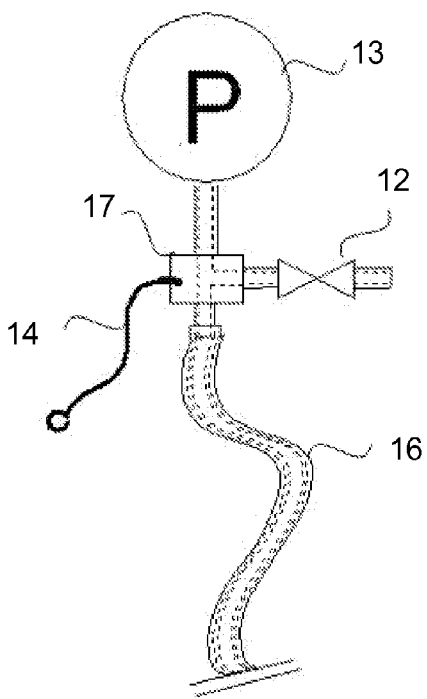
FIG. 6 shows a part of the device according to an alternative embodiment.

FIG. 6 shows a part of the device according to a preferred embodiment, which differs from the device disclosed in FIG. 5 by the fact that it also comprises a flexible pipe conduit 16.

The flexible pipe conduit 16 is arranged to supply pressurized medium to the tubular container (not shown in the figure) of the probe, and is therefore, in one end thereof, connected to the container and, in the other end thereof, connected to means, in the form of a valve 12, in order to supply pressurized medium from a source of pressurized medium. Even if a flexible pipe conduit is shown in FIG. 6, it is also feasible that the pipe conduit is not flexible.

The pipe conduit 16 is preferably a metallic pipe, for instance, a flexible metallic pipe of copper, which is electrically insulated against the surroundings, alternatively a pipe that contains at least one conductor. This allows that means 14 to electrically connect the metallic structure with the tubular container of the probe, for instance, may be arranged in a box 17 placed at a distance from the metallic structure and the container of the probe, the electric connection being obtained via the pipe conduit 16 as well as means for electric connection 14. For instance, said box 17 may be located above the ground in the case when the metallic structure is a pipe conduit installed in the ground.

Figure 7:
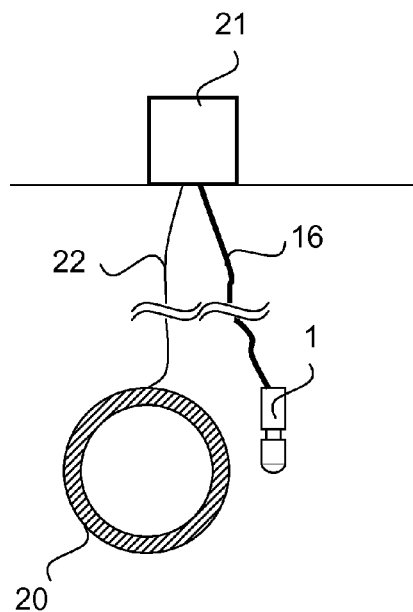
FIG. 7 shows use of the device to indicate a predetermined corrosion of a pipe conduit installed in the ground.

FIG. 7 shows an embodiment when using the device to indicate a predetermined critical corrosion of a pipe conduit 20 installed in the ground. The probe 1 of the device is placed in the vicinity of the pipe conduit 20 installed in the ground and will thereby be subjected to the same or essentially the same external influence as the pipe conduit installed in the ground. A flexible pipe conduit 16, as has been described above reference being made to FIG. 6, is arranged between the probe and a transducer cabinet 21 arranged above the ground. The container of the probe is electrically connected to the pipe conduit 20 installed in the ground via the flexible pipe conduit 16 and an insulated cable 22. This guarantees that the container of the probe has the same electric potential as the pipe conduit 20 installed in the ground.

A pressure gauge to measure the pressure of the pressurized medium is arranged in the transducer cabinet 21. When the container of the probe has corroded so that the container has been perforated, the pressure of the pressurized medium will fall, which is detected by means of the pressure gauge. Thereby, information is obtained about the fact that the corrosion has reached the predetermined critical level, and that it is about time for some type of action on the pipe conduit installed in the ground in order to prevent perforation of the same so that leakage arises.

Figure 8:
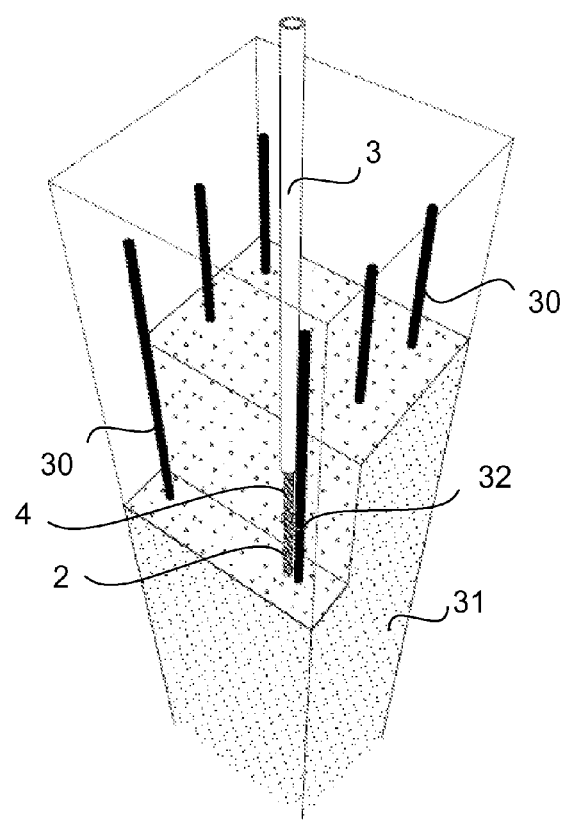
FIG. 8 shows a probe arranged in a concrete structure to indicate a predetermined critical corrosion of reinforcement embedded in said concrete structure.

FIG. 8 shows a partly cropped perspective view of an embodiment when using the device to indicate a predetermined corrosion of a metallic structure in a concrete environment, more precisely reinforcement 30 in concrete 31. At least one part of the probe of the device is cast into the concrete 31 in the vicinity of a reinforcement member 30. The container 2 of the probe is provided with a protective coating 3 except over a surface 4 that is intended to be subjected to corrosion.

According to the figure, the tubular container 2 of the probe is electrically connected to the reinforcement via a staple 32 arranged at the surface 4. However, it is feasible to electrically connect the tubular container in another way, for instance, by means of tying or an insulated electric cable arranged between the reinforcement and the tubular container.

According to a preferred embodiment, a gas that can be detected by means of a gas sensor is used as pressurized medium in the probe, preferably an inert gas. This is, for instance, particularly advantageous when the device is to be used to indicate critical corrosion of reinforcement embedded in concrete, since the probe in these cases may be very long and the corrosion thereby may occur along a long surface. By using a gas, which is detectable by means of a gas sensor, it can easily be detected where the critical corrosion has arisen by using, on the outside of the concrete, such a gas sensor to detect the gas. Said gas sensors are previously known and can in many cases detect very low contents of gases. In this way, information is obtained about where in the concrete structure the corrosion has occurred. The gas sensors may, but do not have to be a part of the device, but may be a separate mobile unit that only is used when the device is has detected that corrosion has occurred.

It should be noted that it is also feasible that another pressurized medium is used in the device until corrosion has occurred, and that the gas that can be detected by a gas sensor then is supplied to the probe in order to, by means of such a gas sensor, thereafter detect where the critical corrosion has been is obtained.

The invention claimed is:

1. Device to indicate a predetermined critical corrosion of a metallic structure, the device comprising a probe that has a closed tubular container intended for a pressurized medium, said container being made of a metallic material and having a centre axis, an outside and an inside as well as a wall thickness (t) that corresponds to the predetermined critical corrosion of the metallic structure, the device furthermore comprising a connection member for the connection of the container to a source of pressurized medium, and a pressure gauge arranged to measure the pressure of the pressurized medium in the container, as well as means for electric connection between the container and the metallic structure, wherein a protective coating is arranged on the outside of said container over essentially the entire outside with the exception of a predetermined surface intended to be subjected to corrosion attack.

2. Device according to claim 1, wherein said tubular container has a first end as well as a second end, and wherein said surface is arranged at a distance from said first end and at a distance from said second end.

3. Device according to claim 1, wherein said tubular container is essentially rotationally symmetrical around said centre axis.

4. Device according to claim 1, wherein said surface has a first extension essentially parallel to said centre axis and a second extension essentially around the entire circumference of the outside of the container.

5. Device according to claim 1, wherein said connection member comprises an electrically insulated pipe conduit arranged between an inlet opening of said container and a valve intended to be connected to a source of pressurized medium.

6. Device according to claim 5, wherein said pipe conduit is flexible.

7. Device according to claim 5, wherein said pipe conduit is metallic alternatively contains a conductor.

8. Method to indicate a predetermined critical corrosion of a metallic structure, wherein the method comprises to arrange a probe in the vicinity of the metallic structure, said probe comprising a closed tubular container having a wall thickness (t) that corresponds to the predetermined critical corrosion, as well as a protective coating arranged on the outside of said container over essentially the entire outside with the exception of a predetermined surface intended to be subjected to corrosion attack, electrically connect the container to the metallic structure, supply pressurized medium to the interior of the container as well as measure the pressure of the pressurized medium in the container, a reduction of the pressure in the container indicating that perforation of the container has occurred, and that the predetermined critical corrosion thereby has been obtained.

9. Use of the device according to claim 1 to indicate a predetermined critical corrosion of a pipe conduit installed in the ground.

10. Use of the device according to claim 1 to indicate a predetermined critical corrosion of a metallic structure embedded in concrete, preferably reinforcement embedded in concrete.

* * * * *